(12) United States Patent
Franklin et al.

(10) Patent No.: US 8,075,537 B2
(45) Date of Patent: Dec. 13, 2011

(54) MULTIPLE CELL THERAPEUTIC DIFFUSION DEVICE

(75) Inventors: Amie B Franklin, Mill Valley, CA (US); Olivier Postel, Redwood City, CA (US)

(73) Assignee: Oxyband Technologies, Inc., Woodbury, MN (US)

( * ) Notice: Subject to any disclaimer, the term of this patent is extended or adjusted under 35 U.S.C. 154(b) by 436 days.

(21) Appl. No.: 12/208,598

(22) Filed: Sep. 11, 2008

(65) Prior Publication Data
US 2010/0042057 A1    Feb. 18, 2010

Related U.S. Application Data

(60) Provisional application No. 61/089,365, filed on Aug. 15, 2008.

(51) Int. Cl.
*A61F 13/00* (2006.01)

(52) U.S. Cl. ........... 604/304; 604/307; 604/308; 602/48

(58) Field of Classification Search .......... 604/304–308; 602/48–51
See application file for complete search history.

(56) References Cited

U.S. PATENT DOCUMENTS

| | | | | |
|---|---|---|---|---|
| 4,666,441 A * | 5/1987 | Andriola et al. | ............... | 424/448 |
| 4,990,144 A * | 2/1991 | Blott | ............... | 604/304 |
| 5,814,031 A * | 9/1998 | Mooney et al. | ............... | 604/307 |
| 6,566,575 B1 * | 5/2003 | Stickels et al. | ............... | 602/41 |
| 6,767,342 B1 * | 7/2004 | Cantwell | ............... | 604/304 |
| 7,799,965 B2 * | 9/2010 | Patel et al. | ............... | 602/48 |
| 2003/0208150 A1 * | 11/2003 | Bruder et al. | ............... | 602/48 |

* cited by examiner

*Primary Examiner* — Lynne Anderson
(74) *Attorney, Agent, or Firm* — Donald R. Boys; Central Coast Patent Agency, Inc.

(57) ABSTRACT

A diffusing device for treating tissue has multiple cells arranged in a cell layer, the cells filled with or charged with a therapeutic agent, an occlusive layer in direct communication with the cell layer, and a diffusion layer in direct communication with the cell layer. In use the diffusing device is sealed peripherally about an area of tissue and therapeutic agent is released from the cells through the diffusion layer based on the diffusion properties of the diffusion layer.

15 Claims, 4 Drawing Sheets

MULTIPLE CELL THERAPEUTIC DIFFUSION DEVICE

CROSS-REFERENCE TO RELATED APPLICATIONS

The present application claims priority to U.S. provisional patent application Ser. No. 61/089,365 filed on Aug. 15, 2008, entitled "Multiple Cell Diffusion Dressing", which is included herein at least by reference.

BACKGROUND OF THE INVENTION

1. Field of the Invention

This invention is in the field of medical technology, and pertains in particular to delivery of oxygen and/or other gasses or compounds to tissue wounds by diffusion.

2. Discussion of the State of the Art

It is by the time of the present application well-known in the art that therapeutic agents may be delivered as gaseous matter to the site of a tissue wound to aid in certain aspects of recovery. Such agents may include for example, antibiotic agents to avoid infection, and delivery of oxygen to speed the healing process. A number of patents have been issued to various inventors that collectively teach local generation of oxygen, for example, at a wound site through bandage systems using chemical reactions, oxygen saturated solutions, or electrochemical generators. Several such patents are listed in an Information Disclosure Statement filed with this patent application.

Supplying Oxygen and other therapeutic agents to a wound site on a continuous and ambulatory basis is therefore known to be of benefit to speed healing and reduce infection. There are still unmet needs in such systems, such as even area distribution of the therapeutic agents to the affected tissue. Thus, more efficient and easier-to-use systems are desirable.

SUMMARY OF THE INVENTION

The problem stated above is that it is desirable for tissue treatment that a dressing is provided with diffusive properties for extended and uninterrupted treatment by one or more therapeutic agents, but current diffusion dressings are unable to provide an evenly distributed therapeutic regimen that is efficiently activated and simple to initiate.

The inventors therefore considered functional elements of therapeutic tissue dressings looking for elements that exhibit specific material properties could potentially be harnessed to provide a diffusion dressing but in a manner that would not create complex or present problems with uneven distribution of therapeutic agent.

The present inventor realized in an inventive moment that if, at the point of application, therapeutic agents could be caused to diffuse more equally and at a better regulated rate, significant improvement in tissue recovery might result. The inventor therefore constructed a unique diffusion dressing for treating tissue that allowed gases to diffuse equally relative to targeted tissue area and at a controlled and uniform rate across the footprint of diffusion, but constrained therapeutic agents save some desired vapor emissions from escaping the dressing in any direction other than into the tissue being treated. A significant therapeutic recovery rate results with no added risk of infection, maceration, dryness, or other tissue healing problems created or elevated.

Accordingly, in one embodiment of the invention a diffusing device for treating tissue is provided comprising multiple cells arranged in a cell layer, the cells filled with or charged with a therapeutic agent, an occlusive layer in direct communication with the cell layer, and a diffusion layer in direct communication with the cell layer. The diffusing device is sealed peripherally about an area of tissue to be treated and wherein the therapeutic agent is released from the cells through the diffusion layer based on the diffusion properties of the diffusion layer.

In one embodiment the therapeutic agent is one of a gas, a gel, or an emulsion containing a gas. In variations of this embodiment the therapeutic agent is one of oxygen, nitric oxide, or carbon monoxide. In one aspect of this embodiment the therapeutic agent includes one or more synthetic drugs.

In a one embodiment the multiple cells are juxtaposed in the cell layer and separated by cell walls. Alternatively, the multiple cells are juxtaposed in the cell layer and separated by cell walls and hollow spaces. In a variation to this embodiment the hollow spaces may be cells filled with an absorbent material.

In one embodiment the diffusion device further has an adhesive perimeter for sealing the device over a targeted tissue area. In one embodiment the diffusing device has a shape with a predicable finite length and a predictable finite width dimension.

Alternatively, the device has an indeterminate shape with at least one dimension being variable depending on cut length.

In one embodiment the diffusing device further has an absorbent layer disposed immediately adjacent to and in front of the diffusion layer, the absorbent layer making intimate contact with the targeted tissue area. In another embodiment the diffusing device including the absorbent layer further includes a backup absorbent layer disposed immediately adjacent to and behind the diffusion layer.

In one embodiment the diffusing device further has multiple perforations strategically located through vertical cell walls of the cells in the cell layer. In a variation of this embodiment the perorations are micro-perforations.

In one embodiment the diffusion layer is one of an organic material or a compound containing organic and synthetic materials. In one embodiment cell layer is one of an organic material treated for impermeability to a therapeutic agent. In one embodiment including an adhesive perimeter, the seal formed by the perimeter is a hermetic seal.

In one embodiment the defusing device further has an additional occlusive layer disposed immediately adjacent to and behind the layer attached over the cell layer wherein the additional layer is manually removable.

According to another aspect of the invention a method is provided for treating an area of tissue using a diffusion device having multiple cells arranged in a cell layer, the cells filled with or charged with a therapeutic agent comprising the steps (a) pre-filling, pre-charging, or preloading, the cell layer of the device with a therapeutic agent, (b) positioning the device over the tissue area to be treated and sizing the device if necessary, and (c) sealing the device to the tissue around a perimeter of the diffusing area of the device.

In one aspect of the method in (a), the therapeutic agent is one of a gas, a gel, or an emulsion containing a gas. In another aspect the therapeutic agent is one of oxygen, nitric oxide, or carbon monoxide. In one aspect the therapeutic agent contains one or more synthetic drugs. In one aspect of the method in (b) the device is sized by cutting a length of the device from a roll of undetermined length.

BRIEF DESCRIPTION OF THE DRAWING FIGURES

DETAILED DESCRIPTION

The inventor provides a device that may be used in an ambulatory fashion to deliver a therapeutic agent, for instance a gas, to a tissue to be treated through a diffusion process. The device enables the targeted tissue to be exposed to the therapeutic agent for a period of time, typically days. The device includes multiple separate cells or reservoirs as opposed to a single cell or reservoir. The present invention is described in enabling detail in the following embodiments.

Figure 1:
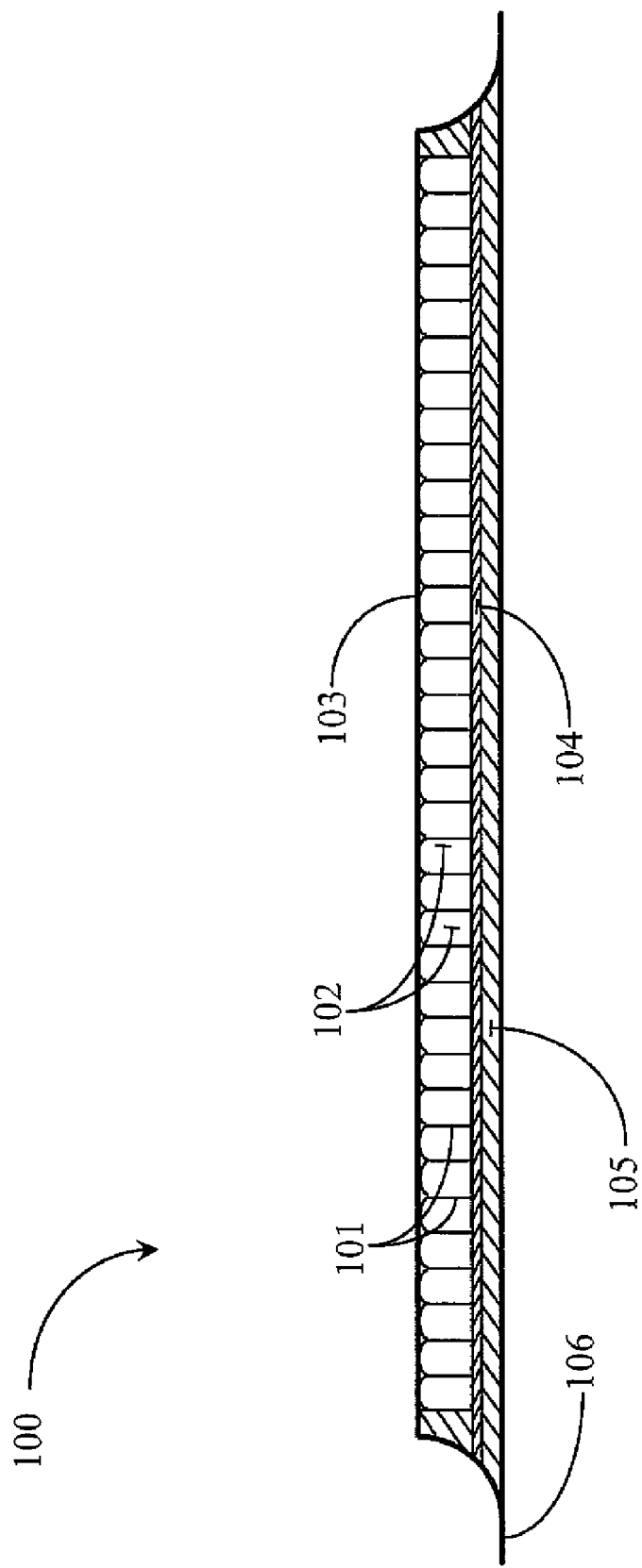
FIG. 1 is a cross-sectional view of a multi-celled diffusion dressing in an embodiment of the present invention.

FIG. 1 is a cross-sectional view of a multi-cell diffusion dressing 100 in an embodiment of the present invention. Diffusion dressing 100 is also termed a diffusion device and may be referred to herein as a device or dressing in its various forms. Device 100 is adapted to deliver a therapeutic agent by diffusing the agent through a specific device diffusion layer 104 that covers the bottom open area of a plurality of cells 101. Cells 101 arranged in a layer may each separately define a volume and may be arranged in a juxtaposed or side-by-side fashion within the layer. Such an array of multiple cells 101 may be ordered in even rows of cells the rows placed side-by-side. The array of cells may also be random or honey-combed. It is not required that all of the cells be exactly the same size with respect to volume definition, wall thickness, shape, or height dimension.

Cells 101 may be manufactured of a polymer-based medical grade material such as polyurethane. Other synthetic materials such as Ethylene-Vinyl Acetate may be used to form the cells. It is preferred that the cells are impermeable to the therapeutic agent stored within each cell volume. In one embodiment an organic cellulose material may be used provided that it is treated for impermeability with respect to leakage of therapeutic agents through the cell walls or cell tops.

Diffusion layer 104 may be manufactured of a permeable material that may be compatible to attachment methods for attaching the diffusion layer directly over the cell openings to enable therapeutic agent 2 to defuse from the reservoirs to the treated tissue over a period of time. In one embodiment, the material is a thin sheet of polyurethane that is made permeable through application of a specific diffusion pattern of micro perforations or openings (not illustrated). Differing patterns, sizes and shapes of perforations may be provided in diffusion layer 104 to regulate the amount of therapeutic agent that reaches the tissue over time. In one embodiment diffusion layer 104 is an organic coating that is porous when set and exhibits the desired diffusion properties. In another embodiment, diffusion layer 104 is a viscous compound of organic and synthetic substances that when mixed and applied as a coating, exhibit the desired diffusive characteristics. Diffusion layer 104 is preferably permeable as described above and allows therapeutic agent 102 to diffuse over periods ranging from minutes to several days, weeks, or longer.

Device 100 may be charged with a therapeutic agent 102 or may be a vehicle through a therapeutic agent is delivered upon subsequent charges. Therapeutic agent 102 may be a gas, such as oxygen, nitric oxide, carbon monoxide, a gel, or an emulsion containing a gas. The therapeutic agent may or may not contain drugs such as antibiotics or other therapeutic drugs used in treatment of tissue wounds. The exact agent and any mediums or additional drug compounds or cocktails used with device 100 may vary as there are many different types of tissue wounds requiring different types of treatments. For example, burns, skin grafts, and infections all remarkably different types of wounds requiring very different treatments.

Device 100 may include an optional occlusive layer 103 that covers the top of the juxtaposed cell layer (101). Layer 103 may be provided to prevent any therapeutic agent from escaping the dressing through the top of the cellular structure if the structure fails to form a tight seal. Layer 103 is made of a material impermeable to the therapeutic agent stored into cells 101. In a preferred embodiment occlusive layer 103 is impermeable to the therapeutic agent, but allows vapor transfer to the outside of the device. Such material can be polyurethane, Ethylene-Vinyl Acetate, or others.

In one embodiment an optional layer 105 may be provided to dressing 100 beneath the diffusion layer 104. Layer 105 is absorbent in a preferred embodiment, but does not change volume when absorption of moisture or other exudates occurs. Layer 105 may contact the skin directly and is porous enough as to not interfere with the diffusive properties of layer 104. Layer 105 may be provided using any synthetic or organic/synthetic material that absorbs liquids but does not significantly change thickness due to absorption. Layer 105 may be impermeable or may have a low permeability to the therapeutic agent. At the same time layer 105 allows vapor transfer from the skin or other tissue to diffuse back through the device. These properties can be realized using a single layer exhibiting all of the properties or a combination of individual layers, each having one of the properties described above.

Device 100 may be applied to a tissue area using an adhesive peripheral layer 106. Layer 106 as an adhesive to hold device 100 in place, is applied to healthy tissue around the tissue targeted for treatment. Standard medical adhesive tape may be used to form this layer around the dressing. The seal prevents any therapeutic agent from escaping to the outside of the dressing.

Figure 2A:
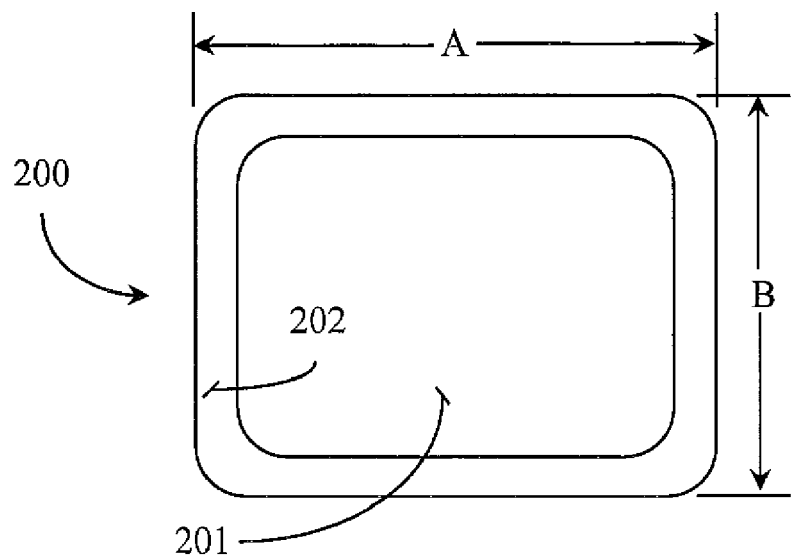
FIG. 2a is a plan view of a dressing according to an embodiment of the present invention, the dressing having a finite shape.
Figure 2B:
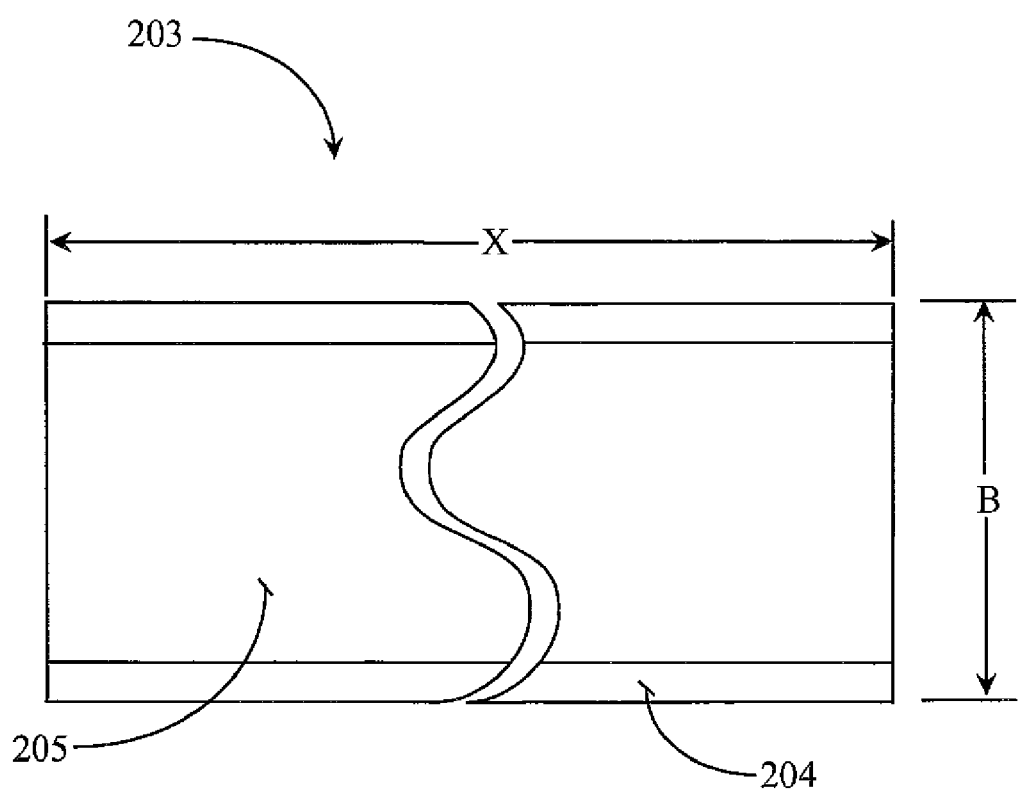
FIG. 2b is a plan view of a dressing according to an embodiment of the present invention, the dressing having a finite shape in one direction, and an undetermined shape in a second direction in the same dimension.

FIG. 2A is a plan view of dressing 200 according to an embodiment of the present invention, the dressing having a dimensionally finite shape. FIG. 2B is a plan view of a dressing 203 according to an alternate embodiment of the present invention, the dressing having an undetermined shape where one dimension is variable.

Referring now to FIG. 2A, dressing 200 is prefabricated in the form of a finite shape like a rounded rectangle or square. Other geometric shapes may be observed as well without departing from the spirit and scope of the invention. In this example, device 200 is a rounded rectangle in geometric footprint. Device 200 includes a footprint 201 where diffusion takes place. Footprint 201 defines the area of the juxtaposed cells described further above. Device 200 has a perimeter footprint 202 where a seal is formed between the device and healthy tissue surrounding the target tissue to be treated. Footprint 202 defines an area of adhesive in the form of tape or treated surface.

Device 200 has a length dimension A and a width dimension B that are both predictable such that the device may be acquired in the desired finite shape having the predictable dimensions. There may be a variety of finite shapes and sizes available in standalone packaging or in assorted collections including devices of varying shapes and sizes.

Referring now to FIG. 2B, device 203 is illustrated having a same width dimension B as the device of FIG. 2A but having a variable length dimension X that is determined by the user. In this case device or dressing 203 may be cut to a determined length X from a roll of material of undetermined length. In this example, a footprint 204 on opposite sides of the device relative to the predictable width B represents the adhesive sealing surface for sealing the device to tissue along those edges. The fact that the device was cut from a roll of material causes a lack of sealing area for the ends of the device assuming two cut lines. Therefore, a user may have to add some adhesive tape to the ends of device 203 for seal purposes. In one embodiment the device may be shaped to size by trimming or cutting and then sealed to an area using sealing adhesive tape adapted for the purpose. In another embodiment to device may be held in place by a wraparound dressing such as gauze, cheesecloth, or a sports wrapping like a soft brace material.

Figure 3:
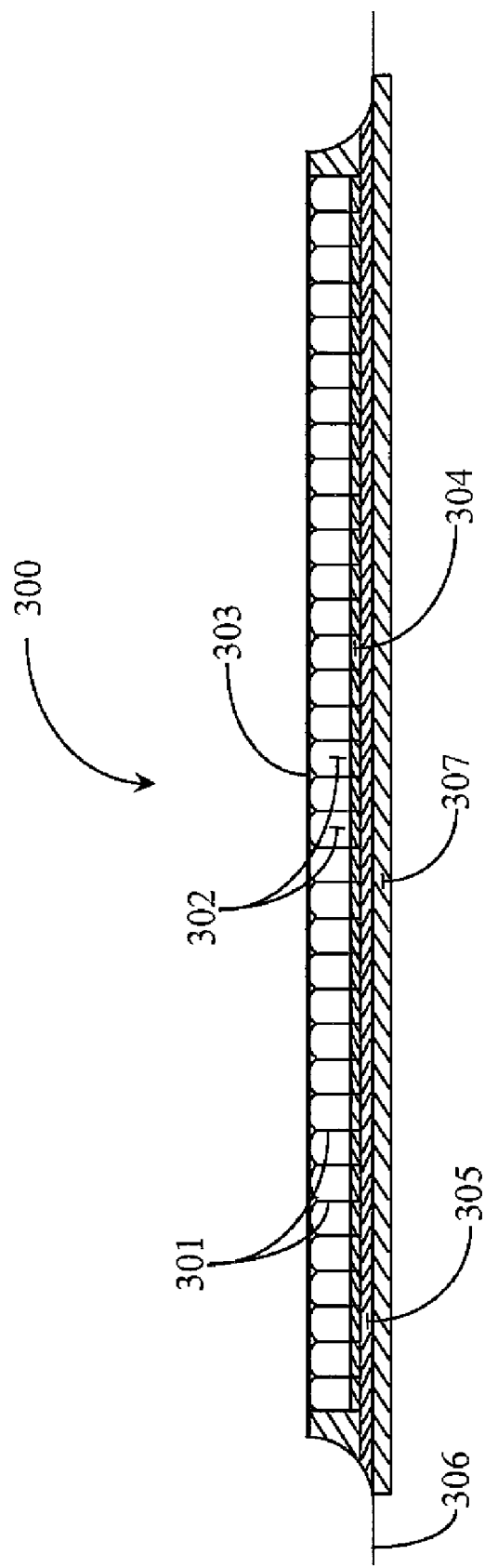
FIG. 3 is a cross-sectional view of a dressing according to an alternative embodiment of the present invention.

FIG. 3 is a cross-sectional view of a dressing 300 according to an alternative embodiment of the present invention. Defusing device 300 includes a layer of cells 301 filled with a therapeutic agent 302 as described further above with reference to FIG. 1 (cells 101, therapeutic agent 102). However, in this case the openings of cells 301 facing a diffusion layer 305 are covered with an absorbent layer 304.

Absorbent layer 304 may be a fast absorbing synthetic or polymer-based material that absorbs moisture including exudates from the targeted tissue area being treated. In this example, diffusion layer 305 is permeable to moisture and exudates from the damaged tissue or wound and allows the absorbent materials to accept the moisture, etc. through the layer. In an optional variation to this embodiment a second absorbent layer 307 may be provided ahead of diffusion layer 305 to make direct contact with the tissue. Absorbent layer 304 may be rated for super absorption in order to provide adequate divertive absorption keeping absorbent layer 307 dry and viable for an extended period. An adhesive layer or sealing layer 3006 is provided around the perimeter of device 300 for sealing the device to preferably healthy tissue.

Figure 4:
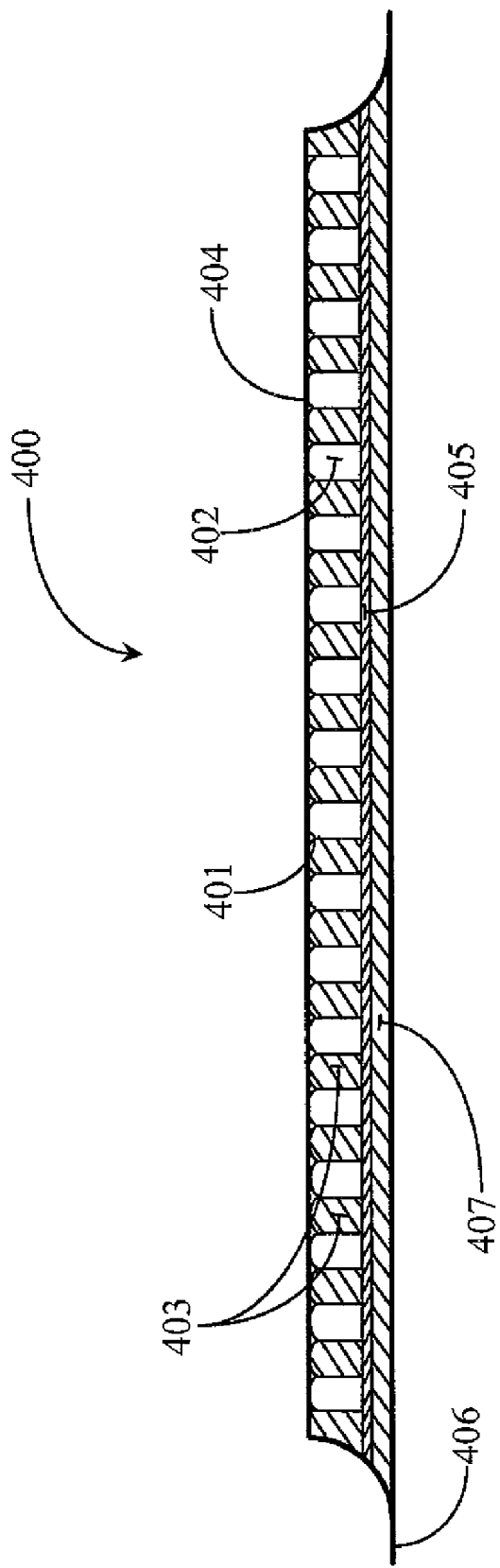
FIG. 4 is a cross-sectional view of a dressing according to another alternative embodiment of the present invention.

FIG. 4 is a cross-sectional view of a dressing 400 according to another alternative embodiment of the present invention. Diffusing device 400 includes a cell layer wherein the individual cells 401 are arrayed in a layer and wherein the cells 401 are filled with a therapeutic agent 402. However, in this embodiment, there is space in-between and surrounding each cell 401 that is filled with an absorbent material 403. The space may be an adjacent cell filled with absorbent material instead of therapeutic agent such that a portion of the cells diffuse therapeutic agent into the targeted tissue while a portion of the cells are engaged in absorbing moisture and exudates from the tissue.

In a variation to the embodiment described above, individual vertical cell walls forming cells 401 may have microperforations or larger perforations strategically placed therethrough to increase the transferability of moisture over the footprint of the diffusing area of the device relative to the absorption cells filled with absorbent material 403. Absorption cells may be symmetrically located throughout the footprint to insure significantly constant absorbent capabilities across the footprint. The perforations may also be present in an embodiment where the cells are all filled with therapeutic agent and only the cell walls separate one cell from another in the cell layer. In this case diffusion properties may be enhanced by restricting but not eliminating altogether cross-migration of therapeutic agents across a diffusion area. Such a diffusion perforation pattern described above may help to equalize gaseous pressure across the device be allowing adjacent cells to communicate with one another in a controlled manner.

Device 400 may be covered on top with a permeation layer 404, which is adapted as a permeation layer for vapor transfer and to prevent bacterial contamination. Device 400 also includes a diffusion layer 405 analogous to those described above. In this example as in other embodiment already described, an optional absorbent layer 407 can be added beneath the diffusion layer for directly contacting the affected tissue. An adhesive layer 406 is analogous to adhesive layers previously described above.

In all embodiments the cell layer material should be impermeable to the therapeutic agent stored therein. The material should however allow transfer of vapors to the outside. A suitable material could be polyurethane, ethylene-vinyl acetate, or other materials. Absorbent materials may be those that absorb moisture and/or exudates from the tissue being treated without changing in volume any significant amount. Top layers such as layer 404 in this example are vapor transfer barriers allowing tissue to dry and preventing maceration. These layers are preferably impermeable to the therapeutic agents.

One with skill in the art of diffusing dressing construction and use will appreciate that there are a variety of ways to layer elements to provide function without departing from the spirit and scope of the present invention. For example, in one embodiment, an occlusive layer (not illustrated) may be provided to cover the top vapor transfer layer and which may be peeled off by a user to activate vapor transfer properties when the device is in use. Also in a preferred embodiment the layer around the edges of the device connecting the top layer to the adhesive layer is occlusive to prevent escape of therapeutic agents.

In another embodiment absorbent layers 105 (FIG. 1), 304 and 307 (FIG. 2), and 403 and 407 (FIG. 4) can be infused or impregnated with a substance such as a biocide, a drug, an antimicrobial agent, an anti inflammatory agent, an analgesic anesthetic or some other pharmaceutical. Such infused chemical agents may be carried along with the diffusion of the therapeutic agent or they may be dissolved (depending on the agent type) in presence of moisture from the tissue. An example of such a process would be the release of chloride dioxide impregnated into any of the above-described absorbent layers to provide antimicrobial properties to the device.

It will be apparent to one with skill in the art that the diffusing device dressing of the invention may be provided using some or all of the mentioned features and components without departing from the spirit and scope of the present invention. It will also be apparent to the skilled artisan that the embodiments described above are exemplary of inventions that may have far greater scope than any of the singular descriptions. There may be many alterations made in the descriptions without departing from the spirit and scope of the present invention.

What is claimed is:

1. A diffusing device for treating tissue comprising:
multiple cells arranged juxtaposed in a cell layer and separated by cell walls and hollow spaces, the hollow spaces filled with an absorbent material, the cells filled with or charged with a therapeutic agent;
an occlusive layer in direct communication with the cell layer; and
a diffusion layer in direct communication with the cell layer;

characterized in that the diffusing device is sealed peripherally about an area of tissue and wherein the therapeutic agent is released from the cells through the diffusion layer based on the diffusion properties of the diffusion layer.

2. The diffusing device of claim 1 wherein the therapeutic agent is one of a gas, a gel, or an emulsion containing a gas.

3. The diffusing device of claim 2 wherein the therapeutic agent is one of oxygen, nitric oxide, or carbon monoxide.

4. The diffusing device of claim 2 wherein the therapeutic agent includes one or more synthetic drugs.

5. The diffusion device of claim 1 further including an adhesive perimeter for sealing the device over a targeted tissue area.

6. The device of claim 5 wherein the seal formed by the adhesive perimeter is a hermetic seal.

7. The diffusing device of claim 1 having a shape with a predicable finite length and a predictable finite width dimension.

8. The diffusion device of claim 1 having an indeterminate shape with at least one dimension being variable depending on cut length.

9. The diffusing device of claim 1 further including an absorbent layer disposed immediately adjacent to and in front of the diffusion layer, the absorbent layer making intimate contact with the targeted tissue area.

10. The diffusing device of claim 9 further including a backup absorbent layer disposed immediately adjacent to and behind the diffusion layer.

11. The diffusing device of claim 1 further including multiple perforations strategically located through vertical cell walls of the cells in the cell layer.

12. The diffusing device of claim 11 wherein the perorations are micro perforations.

13. The diffusing device of claim 1 wherein the diffusion layer is one of an organic material or a compound containing organic and synthetic materials.

14. The diffusing device of claim 1 wherein the cell layer is one of an organic material treated for impermeability to a therapeutic agent.

15. The device of claim 1 further including an additional occlusive layer disposed immediately adjacent to and behind the layer attached over the cell layer wherein the additional occlusive layer is manually removable.

* * * * *